United States Patent [19]
Plummer et al.

[11] Patent Number: 5,240,708
[45] Date of Patent: Aug. 31, 1993

[54] COMPOSITION AND METHOD FOR DISCOURAGING SPIDERS, INSECTS OR THE LIKE

[76] Inventors: Donald E. Plummer; Sonja A. Plummer, both of 10165 NW. 8th La., Ocala, Fla. 32675

[21] Appl. No.: 725,041
[22] Filed: Jul. 3, 1991
[51] Int. Cl.$^5$ .............................................. A01N 25/02
[52] U.S. Cl. ................................. 424/405; 424/195.1; 514/919
[58] Field of Search ............................ 424/405, 195.1; 514/918, 919

[56] References Cited

U.S. PATENT DOCUMENTS

| | | | |
|---|---|---|---|
| 2,159,953 | 5/1939 | Proetto | 424/195.1 |
| 2,196,763 | 4/1940 | Figg | 424/195.1 |
| 4,454,111 | 6/1984 | Boden et al. | 424/58 |

OTHER PUBLICATIONS

Merck Index 1968—pp. 758, 835.
Hinkle et al.—Insecticide & Acaricide Tests: 1988 vol. 13, p. 415, #19K.

*Primary Examiner*—Thurman K. Page
*Assistant Examiner*—Neil Levy
*Attorney, Agent, or Firm*—Allen, Dyer, Doppelt, Franjola & Milbrath

[57] ABSTRACT

A composition and method for spraying an area to inhibit web growth and discourage spiders, other insects or the like from returning to the sprayed area. The solution includes liquid soap that is blended with oil of anise and coriander oil. Capsicum is then added and completely blended in the soap mixture. The mixture is blended with an acetic acid solution to form the solution.

2 Claims, No Drawings

COMPOSITION AND METHOD FOR DISCOURAGING SPIDERS, INSECTS OR THE LIKE

BACKGROUND OF THE INVENTION

This invention relates to a composition of matter for use as a pesticide or pest preventative and a method for making and using the composition. More particularly, this invention relates to a solution of organic materials for inhibiting and discouraging spiders, insects and other pests from reoccurring once sprayed on a surface.

A common problem with many houses and buildings is spider web growth. Spiders tend to congregate in corners of buildings and build webs. Elimination of these webs require constant cleanup by knocking the webs down with brooms and brushes.

Various pesticides and insecticides are available for killing spiders, insects and other bugs to prevent web reoccurrence. However, most pesticides contain toxic materials that are harmful to humans if swallowed. Further, many of the current pesticides only last a short amount of time and must be re-applied to maintain effectiveness. Many pesticides stain surfaces such as walls, carpet, draperies, wallpaper, etc. on contact. Accordingly, these pesticides may not be applicable for indoor use.

SUMMARY OF THE INVENTION

An object of the invention is to provide an improved composition for use in pest control;

Another object of this invention is to mix a composition together that does not contain harmful ingredients and that controls pests;

It is also an object of this invention to combine organic constituents together in a liquid that may be sprayed on an area to discourage insects, spiders or other pests for an extended amount of time;

A further object of this invention is to provide a liquid composition that may be sprayed onto surfaces to inhibit spiders and insets without leaving a stain; and An additional object of this invention is to spray a solution on an area to retard spider web growth.

In a preferred embodiment of the invention, a method of preparing an insect prevention solution is provided. The method is prepared by whipping liquid soap into a foam and then combining oil of anise and coriander oil until blended together in the liquid soap. Liquid capsicum is then added to the coriander oil and anise oil blended soap. Capsicum is then whipped with the blended soap until the liquid capsicum is completely blended into the soap. An acetic acid solution is added to the completely blended soap to complete the process. The solution may then be sprayed on walls, buildings, fences or other structures to prevent reoccurrence of insects, spiders and other pests and retard web growth.

DESCRIPTION OF THE PREFERRED EMBODIMENTS

It has been found that the solution for inhibiting spiders, insects and other pests is contained in the following Table 1. Details of compositions of these materials are listed in *The Source Book of Flavors*, written by Henry Heath, published by A.V.I. of Westport, Conn., 1981 which is hereby incorporated by reference.

TABLE 1

| Ingredient | Location in Source Book of Flavors | Preferred Quantity for One Quart | Proportion of Aqueous Solution | Effective Variance |
| --- | --- | --- | --- | --- |
| Aqueous solution with 1-20% acetic acid: Preferably Distilled White Vinegar | p. 316 (Acetic Acid) | 800 cc | | 790-810 cc |
| Liquid Soap: Preferably Coconut oil based soap | | 44 cc | .05-.111 | 44-89 cc |
| Anise Oil: Oil of *Pimpinella anisum* | p. 220 (Anise) | 3 cc | .0025-0.125 | 1-10 cc |
| Coriander Oil: Oil of *Coriandrum satium* | p. 237 (Coriander) | 1.5 cc | .0018-.00375 | 1.5-3.0 cc |
| Liquid Capsicum: Oleoresin of Capsicum Annum L. | p. 225 (Capsicum) | 1.5 cc | .00125-.00375 | 1.0-3 cc |

The following examples are for preparation of the composition of matter, also referred to as a pesticide solution for inhibiting spiders, insects and pests. Preparation of one liter of the pesticide solution is as follows:

EXAMPLE 1

44.6 cubic centimeters of coconut oil based soap were whipped into a foam, preferably at high speeds for five minutes. About 89 cubic centimeters of oil of pimpinella and anisum (anise oil) and 1.5 cubic centimeters of oil o coriandrum satium (coriander oil) were added to the foam and mixed together at low speeds for approximately five minutes. The mixture was then whipped at high speeds for two minutes. At this time, 1.5 cubic centimeters of liquid capsicum, generally referred to as oleoresin of capsicum annum (capsicum oleoresin) were added and then blended with the other ingredients between five and twenty minutes. The exact blending time is dependent on the viscosity of the soap used. Heavier soaps blend better and quicker than lighter soaps.

This final mixture was whipped until no traces of the capsicum oleoresin remain on the top surface of the substance and become dissolved. 800 cubic centimeters of distilled white vinegar having a 5% acetic acid is added to the blended substance in a small but steady flow. The resulting pesticide must be blended continually during the bottling process for proper consistency of formula.

EXAMPLE 2

Jalapeno peppers were liquified and strained to form a 119 cubic centimeters or 4 ounces of solution. The liquified peppers were substituted for the capsicum in Example 1. In experimentation, the peppers were as effective as the oleoresin of capsicum in discouraging spiders.

EXAMPLE 3

Hot red peppers, cherry peppers, mixed hot peppers and chili peppers were liquified and each individually substituted for the oleoresin of capsicum in Example 1. The 119 cubic centimeters of the liquified peppers were substituted for the capsicum used in Example 1. The end product was effective in discouraging spiders.

EXAMPLE 4

Louisiana hot sauce in one instance and tabasco sauce in another instance were substituted for the oleoresin of capsicum in Example 1. Two ounces or 59 cubic centimeters were substituted for the capsicum used in Example 1. The resulting product was effective in inhibiting spiders.

EXAMPLE 5

Fels Naptha ® soap was melted and a small amount of water was added as it melted. The gel that resulted from this melting process was then used in place of the coconut oil based soap in Example 1. The proportions substituted were equal to the quantity of coconut oil based soap used in Example 1. This soap proved satisfactory in inhibiting spiders and their webs.

EXAMPLE 6

Ivory Liquid Detergent was substituted for the coconut oil based soap in Example 1. The proportions substituted were equal to the quantity of coconut oil based soap used in Example 1. Satisfactory results were obtained in making the dilution as well as using the solution to inhibit spiders and their webs.

EXAMPLE 7

Purex laundry detergent (liquid), Joy dishwashing detergent, Amway's Dish Drops detergent and Arm & Hammer liquid laundry detergent were all individually substituted for the coconut oil based soap in Example 1. The proportion of detergent used was equal to the quantity of coconut oil used in Example 1. Satisfactory results were obtained when making the solution.

EXAMPLE 8

During testing rice vinegar, apple cider vinegar and malt vinegar were substituted for the distilled white vinegar in Example 1. It was determined that the rice vinegar worked to remove webs and discourage spiders from reoccurring. However, apple cider vinegar and malt vinegar removed the webs but did not discourage the spiders from staying away from the area treated. It was recognized that red wine vinegar caused staining of surfaces. Herb vinegars were also substituted for the distilled white vinegar in Example were found to be effective. It was also determined by diluting the vinegar in Example 1 with water caused to be ineffective in both removing webs and discouraging spiders from returning to areas treated.

In this example, aqueous solutions having varying amounts of acetic acid were substituted for the distilled white vinegar in Example 1. It was determined that solutions having acetic acid concentration between 1 and 20% were effective in discouraging spiders.

EXAMPLE 9

The amount of coconut oil based soap was varied between 44 and 89 cubic centimeters in Example 1. It was determined that less than 44 cubic centimeters would result in the product staining surfaces. Adding more than 89 cubic centimeters did not allow the product to mix properly with the acetic acid solution.

EXAMPLE 10

The amount of oil of pimpinella anisum was varied between 1 and 10 cubic centimeters in Example 1. It was determined that less than one cubic centimeter is not effective to discourage spiders from reoccurring and more than ten cubic centimeters overpowers the other necessary ingredients in the pesticide solution.

EXAMPLE 11

The amount of liquid coriander Was varied between 1.5 and 3 cubic centimeters in Example 1. It was determined that using less than 1.5 cubic centimeters of liquid coriander was not effective in discouraging spiders from returning and using more than 3 cubic centimeters results in lung and eye irritation when inhaling fumes from the pesticide solution.

EXAMPLE 12

The amount of oleoresin of capsicum annuum (capsicum oleoresin) was varied between one and three cubic centimeters in Example 1. It was determined that less than one cubic centimeter was not effective in allowing the final product to discourage spiders and that more than three cubic centimeters causes the surfaces to be stained.

Various tests were conducted to determine the effectability of the solution disclosed in Example 1. The results of these tests are as follows:

In a first test, the interior of a lake front home with a heavy infestation of active spiders and web growth was sprayed with the pesticide solution in Example 1. Web-Away was applied to four beams in a heavily infested area approximately 80 square feet each over its entire surface and the webs were removed with a brush. The results were checked for re-growth of webs or spider activity every 30 days with none noticed during eighteen months. After eighteen months it was noticed that a small web was starting to form in a small corner of the ceiling area of the beam.

In another test, a six foot by six foot section of a ceiling area of an exterior wooden porch was sprayed on a lake front home of wooden construction with attached masonry building. This area initially had very high web infestation and spider activity with dirt dauber and wasp nests. The area was treated with the pesticide solution in Example 1. Webs and dauber/wasp nests were removed with a broom.

The area was checked for re-growth of webs, spider activity and resulting dauber/wasp nests every thirty days. No activity or web growth was detected for six months, although adjacent ceiling areas left untreated (has continued activity in web growth). Dauber/wasps began rebuilding nests after three months, but could easily be removed with fingertip to prevent activity.

In another test, an amusement park had to shut down park rides due to wasp activity from nests located on piling supported rides. The pilings were treated with the solution in Example 1.

As of five months after the test, the solution has been successful in preventing wasp activity in areas that were treated.

In another test, a shopping plaza and grocery store in a plaza along with warehouse facilities were treated on their ceilings and roofs. The storefronts and both interior and exterior surfaces of the warehouse facilities were treated with the solution in Example 1. Four months later the area was inspected and the test areas were web free and showed minimal web growth.

Exterior wall and adjoining aluminum soffit and porch area of large plastics manufacturing plant was sprayed with the pesticide solution in Example 1. This area adjoins an area that is lighted 24 hours a day and faces a moderately landscaped oak hammock entrance way and endless acres of undeveloped lands. The spider problem in this area as well as some interiors of the plant became very bad. The area had to be sprayed and fogged to bring the problem under control. The test area was approximately 200 square feet of exterior wall and soffit area adjacent to the same untreated area. The pesticide solution was applied using a compressed air sprayer using approximately ½ gallon of material for the 200 square foot area as the surface was somewhat porous and absorbed some material. The area was rechecked two months later and showed minimal web collection and no spider activity. The untreated adjoining area had live spider activity and heavy web collection.

It was determined that by spraying the pesticide solution onto areas of buildings or other structures inhibits the growth of webs and discourage the recurrence of spiders and wasps from returning.

This concludes the description of the preferred embodiments. A reading by those skilled in the art will bring to mind various changes without departing from the spirit and scope of the invention. It is intended, however, that the invention only be limited by the following appended claims.

What is claimed is:

1. A method for a solution having efficacy in inhibiting spiders from forming webs, comprising the steps of:
   whipping 44-89 parts liquid soap into a foam;
   combining 1 to 10 parts anise oil and 1.5 to 3 parts coriander oil until both are blended together in the liquid soap foam;
   adding 1 to 3 parts liquid capsicum to the coriander oil and anise oil blended soap;
   completely dissolving the liquid capsicum into the blended soap; and
   adding 790-810 parts of an acetic acid solution in a steady flow to the capsicum dissolved blended soap.

2. The method as recited in claim 1 further comprising the step of whipping the liquid capsicum in the blended soap until it completely dissolves.

* * * * *